United States Patent [19]

Sabol et al.

[11] 4,202,781

[45] May 13, 1980

[54] PROCESS FOR MAKING MOLYBDENUM PHOSPHOSULFURIZED HYDROCARBON COMPOSITION

[75] Inventors: Albert R. Sabol, Munster, Ind.; Ernest H. Baughman, Naperville, Ill.

[73] Assignee: Standard Oil Company (Indiana), Chicago, Ill.

[21] Appl. No.: 956,281

[22] Filed: Oct. 31, 1978

[51] Int. Cl.$^2$ .................. C10M 1/48; C10M 3/42; C07F 11/00
[52] U.S. Cl. .................. 252/32.7 HC; 252/46.4; 252/400 A; 260/429 R; 260/429 K
[58] Field of Search .......... 252/32.7 HC, 46.4, 400 A; 260/429 R, 429 K

[56] References Cited

U.S. PATENT DOCUMENTS

| | | | |
|---|---|---|---|
| 2,859,178 | 11/1958 | Forster et al. | 252/32.7 HC |
| 2,900,376 | 8/1959 | Sabol et al. | 252/32.7 HC |
| 3,068,259 | 12/1962 | Hartle | 252/46.4 |
| 3,223,625 | 12/1965 | Cyphers et al. | 252/32.7 HC |

Primary Examiner—Irving Vaughn
Attorney, Agent, or Firm—Mark DiPietro; William T. McClain; William H. Magidson

[57] ABSTRACT

A process for preparing molybdenum phosphosulfurized hydrocarbon compositions by reacting an aqueous solution of a molybdenum compound with a phosphosulfurized hydrocarbon.

8 Claims, No Drawings

PROCESS FOR MAKING MOLYBDENUM PHOSPHOSULFURIZED HYDROCARBON COMPOSITION

This invention relates to a method for preparing molybdenum containing phosphosulfurized hydrocarbon compositions. More particularly, this invention relates to a process of producing molybdenum phosphosulfurized hydrocarbon composition wherein a molybdenum compound in an aqueous medium is reacted with a non-aqueous phosphosulfurized hydrocarbon and the molybdenum depleted aqueous phase is removed. As a result, the molybdenum compounds react with and become chemically bonded to the water-insoluble phosphosulfur groups in the phosphosulfurized hydrocarbon. More specifically, this invention relates to the manufacture of molybdenum phosphosulfurized hydrocarbon compositions which improve the oxidation inhibition, friction modification, and extreme pressure properties of compositions useful for lubrication of internal combustion engines, and other applications.

Molybdenum-containing phosphosulfurized hydrocarbon compositions are well known lubricant additives. U.S. Pat. Nos. 2,758,089 to Hoff and 2,753,306 to Fields disclose processes for the preparation of molybdenum-containing phosphosulfurized polyalkenes comprising the reaction of a molybdenum-containing compound, hydrogen peroxide and a phosphosulfurized polyalkene, optionally, in the presence of a mercaptan or an alcohol. These processes suffer the drawback that the reaction of the phosphosulfurized polyalkene and hydrogen peroxide produce oxidized hydrocarbon constituents which can form deposits on surfaces in the engine reducing engine efficiency. The process appears to have the further drawback that the reaction between the molybdenum compounds and the phosphosulfurized polyalkenes appear to result in mere suspension of the molybdenum compounds in the phosphosulfurized polyalkene. Further, the hydrocarbon insoluble molybdenum compounds react very slowly in the nonaqueous system with the phosphosulfurized polyalkene and require the use of the hydrogen peroxide to promote the suspension of an effective concentration of molybdenum.

U.S. Pat. Nos. 3,140,997 to Price and 3,256,184 to Harting teach a process for the preparation of colloidal molybdenum compounds. The molybdenum compound is extracted from acidified molybdenum-containing solution with a complexing, oxygen-containing solvent such as a ketone or an ether. The extract containing molybdenum compounds is dispersed in an oil containing a phosphosulfurized polyalkene. The extraction solvent is then stripped from the mixture. This process has the drawback that the complexing extraction-solvent produces a molybdenum-solvent complex stable in oil solutions. As a result the complexed solvent cannot be fully stripped during processing. The residual amounts of solvents can produce oxidized by-products that can form deposits on engine surfaces reducing the efficiency of the engine. Further, the solvents discussed in these patents have high boiling points requiring extreme stripping temperatures, often greater then 300° C., resulting in the degradation of the hydrocarbon components of the additive mixtures. This high temperature degradation can result in a lowering of the ability of the compositions to improve lubricant properties. Further, the molybdenum compounds appear to be held in a mere colloidal suspension in the phosphosulfurized polyalkene product rather than as a covalent reaction product with the phosphosulfurized polyalkene.

Dispersions of inorganic metal compounds in lubricants in general suffer the disadvantage that precipitates of the metal compounds can often form in the lubricant dispersions upon standing. This does not occur in compositions of ionically or covalently bonded molybdenum.

The general object of this invention is to provide a new process for producing molybdenum-containing phosphosulfurized hydrocarbon compositions which have improved lubricating properties. A further object of the invention is to produce molybdenum-containing lubricant additives without the use of harmful peroxide promoters or complexing solvents. Still another object of the invention is to provide a process for preparing molybdenum-containing lubricant additive compositions that avoids the use of harmful high temperature reaction conditions. A further object of the invention is to provide a process for the preparation of molybdenum-containing additive compositions in which the molybdenum compound reacts directly with the phosphosulfurized polyalkene agent and does not rely on a mere dispersion of the molybdenum compound in the lubricant.

The objects of this invention can be obtained by reacting an aqueous molybdenum-containing solution with a phosphosulfurized hydrocarbon. We believe that in the reaction of an aqueous molybdenum-containing solution with the phosphosulfurized hydrocarbon at low temperature a direct reaction of the molybdenum compound with the phosphosulfurized hydrocarbon occurs. The molybdenum compounds leave the aqueous phase and enter the non-aqueous hydrocarbon phase. In the presence of the aqueous medium, a colloidal dispersion of the molybdenum compound is apparently avoided. The reaction is believed to produce a molybdenum phosphosulfurized polyalkene reaction product in good yield. In this way, stable molybdenum-containing compositions can be produced without high temperatures, the use of ketone or ether-complexing solvents, or hydrogen peroxide.

Briefly, the molybdenum-containing compositions of this invention are produced by forming an aqueous solution of a molybdenum compound. The molybdenum solution is mixed with a water-insoluble phosphosulfurized hydrocarbon and heated at low temperature to effect the reaction. At the conclusion of the reaction, the aqueous phase depleted of molybdenum is removed and the molybdenum-containing phosphosulfurized polyalkene is obtained.

Molybdenum compounds useful in this invention are those which produce oxides of the molybdenum under reaction conditions. Such compounds include ammonium molybdate, molybdenum oxides and sulfides and the Group I and Group II salts of molybdic acid for example sodium molybdate, potassium molybdate, magnesium molybdate, calcium molybdate, barium molybdate, etc. Molybdenum trioxide is preferable in the invention for reasons of ease of solubility in aqueous solution, reactivity with the phosphosulfurized polyalkene, and availability. Other oxides of molybdenum such as molybdenum dioxide and molybdenum sesquioxide can also be employed. Other molybdenum compounds which can be useful in this invention are discussed in U.S. Pat. Nos. 2,753,306; 2,758,089; 3,140,997; and 3,256,184, which are expressly incorporated by reference herein.

The phosphosulfurized hydrocarbon useful in the invention which are discussed in U.S. Pat. Nos. 2,312,087, and 2,875,188 comprise the product of phosphorus pentasulfide or other commmon phosphosulfides with a hydrocarbon reacted at temperatures from about 90° C. to about 300° C., preferably, about 115° to 200° C. to avoid high temperature degradation, using from about 0.01 to 1.0 equivalents of phosphorus pentasulfide, preferably about 0.5 to 1.0 equivalents of the phosphorus pentasulfide per equivalent of the reactive hydrocarbon. Hydrocarbons reactive with the phosphorus sulfides contain generally aromatic or unsaturated bonds. A non-oxidizing atmosphere is advantageous during the reaction to avoid oxidation. Preferably, an excess of equivalents of the hydrocarbon is used so that the reactive hydrocarbon constituents will react completely leaving no phosphorus pentasulfide in suspension.

A suitable hydrocarbon compound useful in making the phosphosulfurized hydrocarbon can be a synthetic product or a petroleum product derived from refining processes. Examples of these useful hydrocarbons are polymers, bright stocks, residuums, lubricating oils, distillates, petrolatums, paraffin waxes, olefins, aromatics, etc. These hydrocarbons contain reactive portions, generally olefinic and aromatic, and unreactive portions generally paraffinic in nature. Paraffinic constituents can be made more reactive with the use of a halogen promoter.

The hydrocarbon constituent useful in the reaction between the hydrocarbon and the phosphorus pentasulfide can be an olefinic hydrocarbon resulting from the separation of olefins from refinery streams or from the polymerization of low molecular weight mono-olefinic hydrocarbons. The polymers can be obtained by the polymerization of these olefins or mixtures thereof in the presence of a catalyst such as sulfuric acid, boron trifluoride, aluminum chloride, or other similar catalysts of the Friedel-Crafts type.

Preferably olefinic polymers derived from ethene, propene, 1-butene, 2-butene, or isobutylene or mixtures thereof having molecular weights from about 150 to about 50,000 or greater, and preferably from about 300 to about 6,000 are used for reason of economy and reactivity. Such polymers can be obtained by the polymerization in liquid phase of hydrocarbon mixtures containing mono-olefins and other olefinic compounds such as butylene and isobutylene in well known polymerization techniques. For example, the polymerization of isobutylene over aluminum chloride catalysts is a well known procedure. Specific hydrocarbons useful in the reaction with phosphorus pentasulfide include polyisobutylene or polypropene having a molecular weight from 150 to 50,000; dodecene, tetradecene, hexadecene, eicosene, serotene, hectene, etc.

The hydrocarbon phosphosulfurized polybutene composition can be further treated with hot water, steam or wet, heated inert gas, e.g., wet nitrogen at a temperature of 90° C. to 300° C. to improve odor and increase reactivity by hydrolyzing the phosphosulfurized hydrocarbon.

Also contemplated within the scope of the present invention are the reaction products of phosphorus sulfides with aromatic hydrocarbons such as benzene, naphthalene, anthracene, toluene, biphenyl, etc., and alkylated aromatic hydrocarbons such as an alkyl benzene characterized by having an alkyl group wherein the alkyl group has a molecular weight from 300 to 6,000.

The phosphorus-sulfide reactant can be any phosphorus sulfide such as for example $P_2S_3$, $P_4S_3$, $P_4S_7$, and preferably $P_2S_5$ for ease of reaction and availability.

In somewhat greater detail, the molybdenum compound can be dissolved in an aqueous solution prior to reaction with the phosphosulfurized hydrocarbon compound. While molybdenum compounds are generally relatively insoluble in aqueous solutions, solutions of molybdic acid or salts thereof can be prepared. A molybdenum compound is reacted with 1 to about 10 moles of a strong aqueous base per mole of molybdenum compound to produce an aqueous solution of the salt of molybdic acid. Bases useful in preparation of this salt are sodium hydroxide, potassium hydroxide, calcium hydroxide, barium hydroxide, ammonium hydroxide, magnesium hydroxide, etc. Calcium and barium hydroxide produce compounds which have the benefit that filtration is more rapid than products prepared with sodium or potassium hydroxide. Products prepared with sodium and potassium also commonly tend to be somewhat corrosive to valve surfaces. The mixture can be stirred and heated to a temperature up to the boiling point of the water to promote the dissolution. The solution can be cooled. The reaction can be run at the resulting basic pH of the solution or an excess of sulfuric acid is added to the mixture to produce pH in the solution varying from about 1 to 7. Preferably, the pH of the resulting solution ranges from about 1 to about 3.5. The reaction between the phosphosulfurized hydrocarbon can be performed with the aqueous molybdenum solution at a pH from 1-14. At a pH less than 7, the reaction between the molybdenum solution and the phosphosulfurized hydrocarbon is more rapid and molybdenum utilization is increased. We have also found that at the end of the reaction if the aqueous phase is used with a pH less than 3.5 a clear aqueous phase forms rapidly with little or no separation problems. To the aqueous molybdenum-containing solution is charged from about 1 to about 10 moles of the phosphosulfurized hydrocarbon composition per mole of molybdenum compound. The phosphosulfurized hydrocarbon is commonly contained in a lubricating oil or other essentially hydrocarbon diluent to reduce viscosity when necessary. Examples of useful viscosity modifying diluents are aliphatic and aromatic products of the distillation of petroleum such as gasolines, kerosene, naphtha, lubricating oils, etc. Other aliphatic and aromatic solvents commonly useful in preparation of the products can be benzene, toluene, xylene, heptane, octane, isooctane, etc. Oxygen containing solvents have limited utility. Emulsions are commonly caused by the solubility of these solvents in the aqueous phase. The mixture containing the aqueous phase and the organic phosphosulfurized hydrocarbon phase is heated to reflux at a temperature from about 80° to 200° C. and held for a period of time from about 1 hour to about 24 hours until the reaction between the molybdenum compound and the phosphosulfurized hydrocarbon is complete. The aqueous phase can be removed by partitioning or distillation, preferably the aqueous phase is partitioned to avoid leaving impurities in the hydrocarbon phase. The mixture can be heated to strip volatiles and the resulting hydrocarbon phase can be filtered to remove residual solids if necessary.

The process can be performed in either batch or continuous mode. In batch processes, the reactant or reactants with or without solvents may be added to the other reactant(s) in a suitable vessel. In a continuous process, the two reactants in solution or solventless may be charged to a different (counter-current process) or the same reaction zone, e.g., the upper end of a vertical zone maintained at a suitable temperature. The products can commonly be withdrawn from the other end into purification strippers, separators, or filters. At the conclusion of the stripping and filtering, the product is clear and bright containing no solvents. When run in a hydrocarbon, or lubricant oil solvent, the product can be immediately blended into lubricant additive packages.

These molybdenum compositions can be used as lubricating oil additives in various lubricating oils derived from synthetic, animal, vegetable, or mineral oils. Ordinary mineral lubricating oils are preferred for reasons of their availability, general excellence and low cost. This invention also contemplates the presence of other additives in lubricating oils and lubricating oil packages. Such additives include, for example, viscosity index improving agents, pour point depressing agents, antifoam agents, extreme pressure agents, rust inhibiting agents, oxidation and corrosion inhibiting agents, detergents and disperssants. The additive of this invention is generally added to lubricating oils to improve the friction reducing, the load bearing and the anti-oxidant properties of the oil. Depending on the nature of the oil and the intended use differing amounts of the additives are needed in order to be effective. Generally from about 0.1 to about 10 weight percent of the additive or from 0.01 to 5 weight percent of molybdenum is present in the finished lubricant product.

The following examples are illustrative of processes useful in performing the invention and should not be considered as limiting the scope of the invention.

EXAMPLE I

To a 10 gallon batch reactor equipped with an agitator, a nitrogen gas blanket, a heating mantle, and a reflux condenser were charged 608 grams of molybdenum trioxide, 2,400 milliliters of water, 228 grams of a 50% by weight aqueous sodium hydroxide solution. After the mixture was stirred and heated to a temperature of 95° C. to dissolve the molybdenum compound, the solution was cooled to 40° C., and 176 grams of 98 percent sulfuric acid was added. The solution was agitated until the pH throughout the solution was approximately 1. To the reactor was added 11.82 kilograms of a phosphosulfurized polybutene product which was prepared by adding 4,800 grams of polybutene having a molecular weight about 450 to a reactor containing a nitrogen atmosphere, reflux condenser, heating mantle and stirrer. The mixture was heated to a temperature of 105° to 110° C. and nitrogen was passed through the reactor at about 0.5 standard cubic feet per hour. To the reactor was charged 582 grams of phosphorus pentasulfide ($P_2S_5$). The reaction mixture was heated to a temperature of 210° to 215° C. The reaction was continued for 5 hours while maintaining the temperature at about 225° C. The mixture was cooled to a temperature of 171° C. and 2.33 kilograms of diluent 5W oil was added. The mixture was filtered. The phosphosulfurized polyisobutylene had 2.2 weight percent phosphorus, 4.1 weight percent sulfur, a viscosity of about 600 SSU at 100° C. and was clear and bright. Along with the phosphosulfurized polyalkene was added 1.174 kilograms of 5W oil and 8 liters of heptane to convert viscosity. The mixture was refluxed for 6 hours at 85 to 90° C. The product was cooled and the aqueous layer was removed from the reaction vessel. The clear organic layer was heated to 130° C. and stripped with a nitrogen stream. The product contained 1.8 percent molybdenum, 3.2 percent sulfur, 1.8 percent phosphorus and was clear and bright after filtering.

EXAMPLE II

A molybdenum-containing composition was prepared according to the procedure found in U.S. Pat. No. 3,256,184 to Harting discussed above. Into a 5 liter 3 neck flask was charged 88.25 grams of molybdic acid, 225 milliliters of water and 317 grams of reagent grade 36 percent by volume hydrochloric acid. The mixture was stirred at room temperature for 15 minutes to effect solution. The molybdenum compounds were extracted from the acidified solution in a separatory funnel with 613 grams of methylhexyl ketone (2-octanone). The aqueous phase was removed and discarded and the ketone extract was mixed with 375 grams of phosphosulfurized isobutylene as prepared in Example 1. The mixture was stirred for 2 hours at room temperature and then heated to 175° C. under vacuum to remove volatile components including the ketones. The stripped material was filtered and contained 3.6 percent molybdenum, 2.02 percent phosphorus, 4.0 percent sulfur.

EXAMPLE III

Example I was repeated except with 304 grams of molybdenum trioxide, 144 grams of 50% aqueous sodium hydroxide, 88 grams of concentrated sulfuric acid, 6.496 kilograms of the phosphosulfurized polybutene, and 8 liters of isooctane.

EXAMPLE IV

Example III was repeated except with 200 grams of 50% aqueous calcium hydroxide instead of the sodium hydroxide.

EXAMPLE V

Example III was repeated except with 146 grams 50% aqueous magnesium hydroxide instead of the sodium hydroxide.

EXAMPLE VI

Example III was repeated except with 202 grams of molybdenum trioxide instead of the 302 grams.

EXAMPLE VII

Example III was repeated with 44 grams of sulfuric acid instead of the 144 gms and the pH of the aqueous molybdenum solution was 3.5.

TABLE I

| COMPO-NENT | TEST BLENDS | | | | | | | |
|---|---|---|---|---|---|---|---|---|
| | A | B | C | D | E | F | G | H |
| 5X-10W Oil | 92.40 | 91.90 | 91.40 | 92.00 | 91.61 | 91.86 | 91.31 | 91.40 |
| Mannich Dispersant | 5.0 | 5.0 | 5.0 | 5.0 | 5.0 | 5.0 | 5.0 | 5.0 |
| Zn di-octyl Dithiophosphate | 1.0 | 1.0 | 1.0 | 1.0 | 1.0 | 1.0 | 1.0 | 1.0 |
| Overbased Mg Sulfonates | 0.9 | 0.9 | 0.9 | 0.9 | 0.9 | 0.9 | 0.9 | 0.9 |
| Sulfurized Ca Phenate | 0.7 | 0.7 | 0.7 | 0.7 | 0.7 | 0.7 | 0.7 | 0.7 |
| Prod. Ex. I | — | 0.5 | 1.0 | — | — | — | — | — |

TABLE I-continued

| COMPONENT | TEST BLENDS | | | | | | | |
|---|---|---|---|---|---|---|---|---|
| | A | B | C | D | E | F | G | H |
| Prod. Ex. VII | — | — | — | 0.40 | 0.79 | — | — | — |
| Prod. Ex. VI | — | — | — | — | — | 0.54 | 1.09 | — |
| Prod. Ex. II | — | — | — | — | — | — | — | 1.00 |

TABLE II

| TEST BLEND FROM TABLE I | HOT TUBE TEST | |
|---|---|---|
| | $NO_x$ AT 257° C. | AIR AT 202° C. |
| A | 2.4 | 2.0 |
| B | 8.0 | 6.0 |
| C | 8.0 | 6.0 |
| D | 8.0 | 6.5 |
| E | 8.5 | 6.5 |
| F | 8.0 | 6.5 |
| G | 8.0 | 6.0 |
| H | 9.0 | 2.0 |

TABLE III

| TEST BLEND FROM TABLE I | AMIHOT TEST | |
|---|---|---|
| | $W_{pb}$ (mg) | $W_{cu}$ (mg) |
| A | 0 | −0.3 |
| B | −0.2 | −0.5 |
| C | −0.2 | −4.4 |
| D | −0.2 | −1.8 |
| E | −0.3 | −3.4 |
| F | −0.2 | −0.8 |
| G | 0 | −6.5 |
| H | −0.4 | −0.5 |

The hot tube test is a measure of the ability of an oil additive package to resist the formation of deposits caused by the high temperature oxidation of the oil at elevated temperature in the presence of air or nitrogen oxides. In the test a measured amount of oil is slowly metered into a tube maintained at 257° C. or 202° C. Nitrogen oxide or air is passed through the heated tube contacting the oil and causing the oil to react with the gas. A superior oil additive package leaves a lesser deposit on the tube than a poorer oil additive package. The tubes are rated as 10=clean (best) to 0=black and opaque. Table II shows the molybdenum composition produced by the inventive process provides superior resistance to deposit formation in the presence of air than untreated oil and oil containing the prior art material of air and equivalent performance in nitrogen oxides.

The amihot test is a measure of the ability of an oil additive package to resist the corrosive environment present in internal combustion engines that harms metal surfaces, for example, lead and copper bearings. In the test a lead or copper coupon is suspended in a glass tube containing the test oil additive package to which has been added hydrochloric acid. The mixture is heated and air is blown through oil to simulate the acidic-oxidative engine environment. A smaller weight loss from the metal compounds indicates a superior oil additive package. Table III shows that certain of the compounds of the inventive process are superior to a non-treated oil and the prior art molybdenum compound.

TABLE IV

| TEST BLENDS FROM TABLE I | OIL THICKENING TEST 171° C. | | | | | | | |
|---|---|---|---|---|---|---|---|---|
| | AIR AT 60 CC/MINUTE | | | | SPOT DISPERSANCY % | | | |
| | VISCOSITY INCREASE | | | | | | | |
| | 24 HR. | 32 HR. | 40 HR. | 48 HR. | 24 HR. | 32 HR. | 40 HR. | 48 HR. |
| A | 53 | 125 | 421 | 1297 | 93 | 78 | 75 | 59 |
| B | 37 | 59 | 119 | 188 | 96 | 90 | 88 | 75 |
| C | 45 | 62 | 74 | 120 | 97 | 95 | 90 | 84 |
| D | 37 | 68 | 124 | 274 | 95 | 90 | 82 | 75 |
| E | 31 | 58 | 89 | 127 | 98 | 96 | 89 | 83 |
| F | 34 | 42 | 75 | 124 | 98 | 93 | 90 | 82 |
| G | 29 | 43 | 56 | 95 | 98 | 95 | 91 | 86 |
| H | 55.3 | 57.9 | 121.1 | 442 | | | | |

Antioxidative properties of oil composition were measured by an oil thickening test. In this test 100 grams of test oil are oxidized at 280° F. in an open oxidation tube, while being blown with 60 cc air/minute. Oxidation is catalyzed by the addition of 5 wt% Ford VC sludge oil. Samples are taken periodically and the viscosity is determined. The ability of an additive to maintain low viscosity is highly desirable. Also, a sample of this oil after 48 hours of oxidation is run in the Spot Disperancy Test which gives a measure of the oil's ability to disperse sludge and varnish. In the Spot Dispersancy Test, 3-10 drops of oil are placed onto a standard white blotter paper on which is a sludge spot. After 24 hours, the diameter of the sludge spot and the oil spot are measured. Dispersancy is reflected by the ability of an oil to keep sludge in suspension. Thus, dispersancy will be reflected by the difference in diameters of the sludge and oil spots. A rating (SDT Rating) is given by the diameter of the sludge spot divided by the diameter of the oil spot, and multiplied by 100. A high numerical rating indicates good dispersancy. In a superior additive-oil package the dispersancy will remain high. The superior ability of the molybdenum compound of this invention to maintain low viscosity and high dispersancy is shown in Table IV.

The property of an additive to reduce the friction between lubricated moving parts in an engine is measured by the motored engine test. In the test an oil additive package is placed in a thermostated engine driven by an electric motor. The engine is heated to various temperatures and the horsepower required to overcome the friction inherent in the engine is measured. The lower the horsepower the better the additive. Table V shows the product of the claimed process is superior to the product of the prior art in reducing friction in the engine and the prior art material is roughly equivalent to an untreated finished oil.

TABLE V

| MOTORED OLDSMOBILE ENGINE TEST | | | | | | | |
|---|---|---|---|---|---|---|---|
| FINISHED OIL** CONTAINING PROD. OF EX. | FRICTION HORSEPOWER AT OIL TEMP. (°C.) | | | | | | |
| | 38° | 60° | 82° | 93° | 104° | 116° | 127° |
| * | 11.98 | 10.47 | 10.05 | 10.00 | 10.15 | 10.59 | — |

TABLE V-continued

MOTORED OLDSMOBILE ENGINE TEST

| FINISHED OIL** CONTAINING PROD. OF EX. | FRICTION HORSEPOWER AT OIL TEMP. (°C.) | | | | | | |
|---|---|---|---|---|---|---|---|
| | 38° | 60° | 82° | 93° | 104° | 116° | 127° |
| II | 11.97 | 10.57 | 10.15 | 9.97 | 9.90 | 10.06 | — |
| I | 10.85 | 10.48 | 9.82 | 9.66 | 9.55 | 9.48 | — |
| MOTORED PINTO ENGINE TEST | | | | | | | |
| * | 9.82 | 8.78 | 8.22 | 8.10 | 8.21 | 8.29 | 8.32 |
| II | 9.60 | 8.63 | 8.12 | 8.05 | 8.15 | 8.23 | 8.38 |
| I | 9.53 | 7.99 | 7.85 | 7.85 | 7.85 | 7.85 | |

*Baseline
**Oils contain 0.048 (wt)% molybdenum based on total weight of oil.

I claim:

1. A method for preparing a molybdenum-containing phosphosulfurized hydrocarhon composition which comprises reacting an aqueous solution of a molybdenum compound with a phosphosulfurized hydrocarbon and removing substantially all the water.

2. The method of claim 1 wherein the phosphosulfurized hydrocarbon comprises a phosphosulfurized polyalkene wherein the polyalkene has a molecular weight from about 300 to about 6,000.

3. The method of claim 2 wherein the phosphosulfurized hydrocarbon is hydrolyzed prior to reaction with the molybdenum solution.

4. The method of claim 1 wherein the molybdenum solution used to prepare the molybdenum containing phosphosulfurized hydrocarbon is acidic and is prepared by reacting at least one molybdenum containing compound selected from the group consisting of molybdenum trioxide, alkaline metal molybdate, and ammonium molybdate with at least one aqueous strong base selected from the group consisting of sodium hydroxide, potassium hydroxide, calcium hydroxide, barium hydroxide, ammonium hydroxide, and acidifying the resulting composition with a strong mineral acid to a final pH of the composition between 1 and 7.

5. The method of claim 1 wherein the phosphosulfurized hydrocarbon composition is dissolved in at least one inert hydrocarbon selected from the group consisting of lubricating oils, hexane, heptane, octane, isooctane, and nonane prior to reaction with the molybdenum solution, 6. The product of the method of claim 1.

7. A method for preparing a molybdenum containing phosphosulfurized hydrocarbon composition which comprises reacting at least one molybdenum containing compound selected from the group consisting of molybdenum trioxide, molybdenum dioxide, molybdenum sesquioxide, molybdenum sulfuide, alkaline metal molybdate, and ammonium molybdate, with at least one aqueous base selected from the group consisting of sodium hydroxide, potassium hydroxide, calcium hydroxide, magnesium hydroxide, and ammonium hydroxide; and a phosphosulfurized polyalkene; and removing substantially all the water.

8. A lubricant containing the product of the method of claim 1.

* * * * *